United States Patent [19]

Liang et al.

[11] Patent Number: 5,872,160
[45] Date of Patent: Feb. 16, 1999

[54] DENTURE STABILIZING COMPOSITIONS

[75] Inventors: Nong Liang, West Chester; Jayanth Rajaiah, Loveland; Kimberly Ann Gilday-Weber, Cincinnati, all of Ohio

[73] Assignee: The Procter & Gamble Company, Cincinnati, Ohio

[21] Appl. No.: 835,040

[22] Filed: Mar. 27, 1997

[51] Int. Cl.⁶ .............. A61K 6/00; A61C 13/23; C09J 7/00
[52] U.S. Cl. .............................................. 528/120
[58] Field of Search ................................ 523/120

[56] References Cited

U.S. PATENT DOCUMENTS

| | | | |
|---|---|---|---|
| 2,866,775 | 12/1958 | Sellers | 260/78.5 |
| 2,897,593 | 8/1959 | Hollander et al. | 32/2 |
| 3,575,915 | 4/1971 | Novak et al. | 260/29.6 |
| 3,736,274 | 5/1973 | Schoenholz et al. | 260/17 R |
| 3,983,095 | 9/1976 | Bashaw et al. | 526/15 |
| 3,990,149 | 11/1976 | Nedwig | 433/186 |
| 4,136,163 | 1/1979 | Watson et al. | 424/54 |
| 4,202,098 | 5/1980 | Russo | 433/168 |
| 4,373,036 | 2/1983 | Chang et al. | 523/120 |
| 4,393,080 | 7/1983 | Pawelchak et al. | 428/355 |
| 4,503,116 | 3/1985 | Lapidus | 428/286 |
| 4,514,528 | 4/1985 | Dhabhar et al. | 523/120 |
| 4,529,748 | 7/1985 | Wienecke | 523/120 |
| 4,530,942 | 7/1985 | Dhabhar et al. | 523/118 |
| 4,569,955 | 2/1986 | Dhabhar | 523/120 |
| 4,632,880 | 12/1986 | Lapidus | 428/523 |
| 4,680,319 | 7/1987 | Gimpel et al. | 523/210 |
| 4,758,630 | 7/1988 | Shah et al. | 525/207 |
| 4,772,470 | 9/1988 | Inoue et al. | 424/435 |
| 4,880,702 | 11/1989 | Homan et al. | 428/354 |
| 4,980,391 | 12/1990 | Kumar et al. | 524/45 |
| 5,049,235 | 9/1991 | Barcus et al. | 162/9 |
| 5,073,604 | 12/1991 | Holeva et al. | 525/327.8 |
| 5,093,387 | 3/1992 | Schobel et al. | 523/120 |
| 5,106,914 | 4/1992 | Russell et al. | 525/384 |
| 5,158,825 | 10/1992 | Altwirth | 428/286 |
| 5,166,233 | 11/1992 | Kuroya et al. | 524/37 |
| 5,204,414 | 4/1993 | Pelah et al. | 525/327.8 |
| 5,209,777 | 5/1993 | Altwirth | 106/35 |
| 5,239,017 | 8/1993 | Pelesko et al. | 525/383 |
| 5,369,145 | 11/1994 | Gasman et al. | 523/120 |
| 5,525,652 | 6/1996 | Clarke et al. | 524/37 |
| 5,543,443 | 8/1996 | Rajaiah et al. | 528/120 |
| 5,658,586 | 8/1997 | Rajaiah et al. | 528/420 |

FOREIGN PATENT DOCUMENTS

| | | | |
|---|---|---|---|
| 0353375 | 2/1990 | European Pat. Off. | A61C 13/23 |
| 0 555 019 A1 | 8/1993 | European Pat. Off. | A61K 6/00 |
| WO 97/20520 | 6/1997 | European Pat. Off. | A61C 13/23 |
| 3613432 | 10/1987 | Germany | A61C 13/23 |
| 58-027766 SHO | 2/1983 | Japan | C09J 3/14 |
| 63-54318 | 3/1988 | Japan | A61K 9/70 |
| 4-149110 | 5/1992 | Japan . | |
| 5-65210 | 3/1993 | Japan . | |
| 6-65211 | 3/1993 | Japan . | |
| WO 96/04883 | 2/1996 | WIPO | A61K 6/087 |

*Primary Examiner*—Shep K. Rose
*Attorney, Agent, or Firm*—Betty J. Zea; Mary Catherine Hentz; Jacobus C. Rasser

[57] ABSTRACT

Disclosed is a denture adhesive composition comprising at least one non-adhesive self-supporting layer; and a partial salt of a lower alkyl vinyl ether-maleic acid copolymer, the partial salt copolymer comprising carboxyl groups, of which from about 50% to about 95% are neutralized by one or more metal cations; wherein the partial salt copolymer is covalently crosslinked with an organic crosslinker and wherein the molar ratio of organic crosslinker to carboxyl groups, prior to neutralization by the metal cations, is from about 0.1% to about 30%.

20 Claims, No Drawings

DENTURE STABILIZING COMPOSITIONS

BACKGROUND OF THE INVENTION

Ordinary removable dentures, dental plates and the like, comprise teeth mounted in a suitable plate or base. Denture adhesives or stabilizers are used to provide a cushion or gasket between the denture and the gums or tissues and to fill the interstices between the dentures and the gums or tissues.

Denture stabilizing or adhesive compositions can exhibit several deficiencies. Aesthetic deficiencies may include oozing of the adhesive from under the dental plate during insertion and throughout the wearing period and messiness and difficulty of removing the residual adhesive from the mouth and dentures. Additionally, food may become trapped between the denture and the oral cavity of the wearer. Considerable effort has been made over the years to develop denture adhesive compositions with improved holding capabilities which are aesthetically pleasing and easy to use.

Lower alkyl vinyl ether-maleic copolymers and salts thereof are known in the art for use in denture adhesive compositions. Such disclosures include: U.S. Pat. No. 4,980,391 to Kumar et al., issued Dec. 25, 1990; U.S. Pat. No. 5,073,604 to Holeva et al., issued Dec. 17, 1991; and U.S. Pat. No. 5,525,652 to Clarke, issued Jun. 11, 1996.

Technologies comprising crosslinked alkyl vinyl ether-maleic copolymers providing absorbent fibers and adhesives have also been taught in the art. Examples include: U.S. Pat. No. 3,983,095 to Bashaw et al., issued Sep. 28, 1976, disclosing a method for preparing water-insoluble, water-swellable fibers by reacting a copolymer of maleic anhydride and a cross-linking agent; U.S. Pat. No. 2,866,775 to Sellers, issued Dec. 30, 1958, disclosing adhesive compositions comprising esters of maleic anhydride and vinyl ether copolymers optionally crosslinked with glycols; and U.S. Pat. No. 5,049,235 to Barcus et al., issued Sep. 17, 1991, disclosing absorbent fibers comprising a cellulosic fiber, a poly(methyl vinyl ether-co-maleate) copolymer and a polyol, all of which are chemically bonded together. Layered denture adhesive compositions have also been disclosed in, for example, U.S. Pat. No. 4,880,702 to Homan et al., issued Nov. 14, 1989 and European Patent Application 0,353,375 to Altwirth, published Feb. 7, 1990.

Despite the above-noted technologies, as well as others, a need still exists for denture stabilizing compositions providing improved hold and aethestics.

In accordance with the present invention, it has been discovered that denture adhesive compositions comprising a non-adhesive self-supporting layer and partial salts of lower alkyl vinyl ether-maleic acid copolymers lightly crosslinked covalently with an organic crosslinker provide superior denture stability and retention over a significantly longer period of time versus conventional denture adhesives. Specifically, the compositions exhibit higher resistance to salivary washout while maintaining the same or better denture hold as conventional denture adhesives. This added resistance to salivary washout translates to longer denture hold and stability. It is believed that the low level of covalent crosslinking of the partial salt of a lower alkyl vinyl ether-maleic acid copolymer distinguishes the present invention from other technologies utilizing crosslinked alkyl vinyl ether-maleic acid copolymers or their partial salts.

Therefore, it is an object of the present invention to provide partial salt lower alkyl vinyl ether-maleic copolymers which are lightly crosslinked with an organic crosslinker, which are delivered on a non-adhesive self-supporting layer vehicle. It is also an object of the invention to provide an improved adhesive compositions which may be used with dentures and provide a firm hold and exhibit higher resistance to salivary washout.

These and other objects of the present invention will become readily apparent from the detailed description which follows.

SUMMARY OF THE INVENTION

The present invention relates to a denture adhesive composition comprising at least one non-adhesive self-supporting layer; and a partial salt of a lower alkyl vinyl ether-maleic acid copolymer, the partial salt copolymer comprising carboxyl groups, of which from about 50% to about 95% are neutralized by one or more metal cations; wherein the partial salt copolymer is covalently crosslinked with an organic crosslinker and wherein the molar ratio of organic crosslinker to carboxyl groups, prior to neutralization by the metal cations, is from about 0.1% to about 30%.

DETAILED DESCRIPTION OF THE INVENTION

The denture adhesive compositions of the present invention comprise a partial salt of a lower alkyl vinyl ether-maleic acid copolymer covalently crosslinked with an organic crosslinker and a non-adhesive self-supporting layer. The adhesive compositions are thoroughly moistened and applied to dentures. The attachment of the adhesive component to the non-adhesive self-supporting layer provides a composition which may ooze less in the oral cavity than conventional adhesive creams which contain oily carrier vehicles. This attachment also provides a composition which is easy to clean from dentures since the non-adhesive self-supporting layer maintains its strength and integrity in the presence of water and/or saliva, and allows the composition to be peeled from the dentures upon their removal. A detailed description of essential and optional components of the present invention is given below.

Partial Salt of a Lower Alkyl Vinyl Ether-Maleic Acid Copolymer

The lower alkyl vinyl ether-maleic acid ("AVE/MA") copolymer consists essentially of the repeated structural unit:

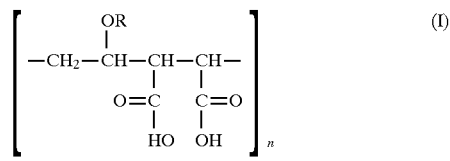

wherein R represents a C1 to C4 alkyl radical, n is an integer greater than one representing the number of repeated occurrences of the structural unit in a molecule of the copolymer. In characterizing the copolymer, n is large enough such that the specific viscosity of the copolymer is larger than 1.2, the specific viscosity being determined in methyl ether ketone at 25° C.

Lower alkyl vinyl ether maleic polymers are readily obtained by copolymerizing a lower alkyl vinyl ether monomer, such as methyl vinyl ether, ethyl vinyl ether, divinyl ether, propyl vinyl ether, isobutyl vinyl ether and the like, with maleic anhydride to yield the corresponding lower alkyl vinyl ether-maleic anhydride copolymer which is readily hydrolyzable to the acid copolymer. In general, the resulting copolymer is a 1:1 copolymer. Both anhydride and acid forms are also available from commercial suppliers. For example, ISP Technologies Inc. ("ISP"), Wayne, N.J., provides both the polymeric free acid form (1) and the corresponding anhydride form under its "GANTREZ" trademark as the "GANTREZ S Series" and "GANTREZ AN Series", respectively. In the former acid series, the GANTREZ S-97 is particularly suitable, and, in the latter anhydride series, the GANTREZ AN-149 (specific viscosity of 1.5 to 2.5) the GANTREZ AN-169 (specific viscosity of 2.6 to 3.5) and the GANTREZ AN-179 (specific viscosity of 3.5 to 5.0) copolymers are particularly suitable. These copolymers are described in greater detail in U.S. Pat. No. 5,395,867 to Prosise, issued Mar. 7, 1995; which is incorporate herein by reference in its entirety. When the anhydride copolymer dissolves in water, the anhydride linkage is cleaved so that the highly polar, polymeric free acid (I) is formed. Accordingly, the anhydride form, which is relatively less expensive than the acid form, may be used as a convenient and cheaper precursor for the acid. Elevated temperatures may be advantageously employed to enhance the rate of anhydride-to-acid hydrolysis.

The anhydride form of copolymer is particularly useful in this invention. The said covalent crosslinking occurs through opening the anhydride with an organic crosslinker. The acid form of the copolymer can be converted back to the anhydride form at elevated temperature and upon removal of water from the polymer.

The lower alkyl vinyl ether-maleic ("AVE/M") polymers useful in the present invention are partial copolymer salts. The partial salt form of the copolymer comprises at least one type of metal cations which are available for neutralization of the carboxylic acid groups of the copolymer. Suitable metal cations may be monovalent, polyvalent (i.e., divalent and trivalent metal cations) or mixtures thereof. Such metal cations include calcium, sodium, magnesium, potassium, ammonium, zinc, strontium, aluminum, iron, and mixtures thereof. Preferred are zinc, strontium, magnesium, iron, aluminum, calcium, and sodium, and mixtures thereof. Most preferred are zinc, iron and calcium. Partial salts of lower alkyl vinyl ether-maleic acid polymers are also described in U.S. Pat. No. 5,073,604 to Holeva et al., issued Dec. 17, 1991; U.S. Pat. No. 4,980,391 to Kumar et al., issued Dec. 25, 1990; and U.S. Pat. No. 5,525,652 to Clarke, issued Jun. 11, 1996; all of which are incorporated herein by reference.

The copolymer salts may be mixed or unmixed or both. The term "unmixed polymer salts" as used herein refers to salts of lower alkyl vinyl ether-maleic polymers wherein the cations are unmixed with any other ester functions or nonidentical cations on the same polymer, the remaining carboxyl groups being unreacted.

The term "mixed polymer salts" as used herein refers to salts of the lower alkyl vinyl ether-maleic polymers where different cations are mixed on the same polymer with each other or with other ester functions. Preferred are mixed polymer salts containing zinc and calcium cations.

The salt form of the subject copolymers can be prepared by the interaction of the AVE/M anhydride polymer with at least one type of metal cation, such as zinc, strontium, calcium, sodium, magnesium, potassium, aluminum, iron, or ammonium compounds having a functional group typical of reactants of a carboxylic acid; such as, for example, the hydroxide, acetate, halide, lactate, etc. in an aqueous medium. In a preferred embodiment, the oxide of zinc, the hydroxide of calcium, and the sulfate of iron are utilized. Since zinc hydroxide is not commercially available, its use as a reactant is readily and more economically accomplished by employing an aqueous slurry of particular zinc oxide which, although practically insoluble in water, provides hydration to zinc hydroxide on the particulate surface.

The sum total of metal cations in the resultant partial salt of AVE/M copolymers should be sufficient to give a neutralization ranging from about 0.1% to about 75% of the metal cations selected from the group consisting of aluminum, iron, zinc, strontium, calcium, sodium, magnesium, potassium, ammonium, and mixtures thereof. The resulting partial copolymer salts contain free acid in the range of from about 5% to about 50%.

Preferred partial copolymer salts comprise zinc from about 10% to about 65%, preferably from about 5% to about 45%, and most preferably from about 10% to about 30%, of the initial carboxyl groups reacted; and calcium and/or strontium each from about 10% to about 75%, preferably from about 25% to about 60%, and most preferably from about 40% to about 60%, of the total initial carboxyl groups reacted. Also preferred are partial copolymer salts comprising iron from 0.1% to about 10%, preferably from about 0.5% to about 5%, and most preferably from about 0.5% to about 3%, of the initial carboxyl groups reacted. Copolymer salts comprising sodium from about 1% to about 20%, preferably from about 1% to about 15%, and most preferably from about 1% to about 10%, of the total initial carboxyl groups reacted, are also preferred.

Cations that form toxic, irritating or contaminating by-products should be avoided, or special precautions and treatment provided to assure the removal and absence of such by-products from the polymeric salt end-product. The particular compound used should be substantially pure to assure obtaining a substantially pure, substantially off-white copolymeric salt end-product. The partial salt copolymers are utilized in the present composition in an amount of at least 10 percent and more preferably in amount of at least 20 percent, by weight of the adhesive composition.

Organic Crosslinker

The organic crosslinker is at least partially chemically incorporated by reaction with maleic anhydride moieties of the copolymer so that it is no longer in the free state and acts as a crosslinking group in the adhesive. Suitable organic crosslinkers include polyols, polyamines, and compounds containing at least two mixed functional groups. Each of these classes of compounds has at least two functional group which are available to covalently crosslink with a carboxyl group of the copolymer, e.g. polyols, -hydroxyl; and polyamines, -primary or secondary amines.

Polyols suitable herein are organic molecules consisting essentially of carbon, hydrogen and oxygen and have two or more —OH groups. While a wide variety of polyols are useful herein, preferred polyols are diols, especially water-soluble diols. Preferred diols are selected from the group consisting of polyethylene glycol, alkane diols, polyethylene-polypropylene block copolymers, poloxamers, and the like.

In more preferred embodiments, the polyol is a polyethylene glycol, (commonly known as "PEG"), which can have varying molecular weight. Polyethylene glycol has the formula $HO(CH_2CH_2O)_nH$ wherein n is greater than or equal to 4. PEG compounds are commercially available under the trade name Carbowax and sold by Union Carbide, Carleston, W.V. Preferred embodiments of these materials are found in the commercial PEG series having average molecular weights of from about 200 to about 1000. More preferred are PEG having average molecular weights of from about 200 to about 600. PEG having average molecular weight of about 300 is most preferred for use herein.

Polyamine compounds suitable for use herein include primary or secondary polyamines, preferably diamines of C12-C18, such as polyoxyethylenated 1,12-dodecanediamine. Water soluble diamines are preferred such as polyoxyethylenated diamines.

Proportions of Components

The proportion of organic crosslinker to carboxyl groups of the partial salt copolymer is described herein in terms of the molar ratio of organic crosslinker functional groups to carboxyl groups of the partial copolymer salts. Therefore, when used herein, the percentages for "molar ratio of organic crosslinker" refer to molar ratio of organic crosslinker functional groups, which are available to covalently crosslink with the carboxyl groups of the partial copolymer salts prior to neutralization, the number of such functional groups then divided by two.

The molar ratio of organic crosslinker to carboxyl groups is from about 0.1% to about 30%, preferably from about 1% to about 20%, most preferably from about 2% to about 10%. Without being bound by theory, it is believed that the proportion of copolymer to organic crosslinker is very important for controlling the crosslink density in the present adhesive invention. The above-cited ranges take into account that maintaining a relatively constant, low crosslink density is preferred.

The low covalent crosslinking density, co-existing non-covalent crosslinking with polyvalent metal cations and moderate chain length of the organic crosslinker provide several physical properties which characterize the present invention. First, the copolymers are water insoluble and exhibit limited water uptake while maintaining high adhesive tensile strength under washout in a modified commercial adhesive block test. Second, the adhesive copolymers form brittle flakes when dried. The adhesive copolymers have no appreciable cohesive strength, (i.e., they do not form a highly cohesive mass, either in a dried form or after activation by moisture, which is moldable and/or peelable). They are easily ground to a fine powder form which can be activated by moisture and/or combined with conventional denture adhesive delivery vehicles to a desired product form. Third, after activation with moisture, the adhesive copolymers offer improved spreading and lubricity.

Non-Adhesive Self-Supporting Layer

The present denture adhesive compositions comprise at least one non-adhesive self-supporting layer. The non-adhesive self-supporting layer is characterized by its ability to maintain strength and provide integrity for the adhesive composition in the presence of water and/or saliva. The non-adhesive self-supporting layer may include such materials as polyester, polypropylene, nylon, rayon, polyethylene oxide, cellulose acetate, cellulose derivatives, cloth, fibrous fleece, paper, plastic, leather, microcrystalline wax, synthetic fibers, natural fibers, and mixtures thereof. Preferred are cellulose derivatives, polyester, polypropylene, nylon, rayon, cloth, paper, microcrystalline wax, and mixtures thereof. Most preferred are polyester, polypropylene, rayon, nylon, cloth and paper.

The non-adhesive self-supporting layer may be in any physical form suitable for providing strength and/or integrity to the present adhesive compositions. Such physical forms include non-woven, woven, continuous, chopped, and combinations thereof. In addition, the non-adhesive self-supporting layer may be formed by any process commonly known in the art. Such processes include un-bonded, spraybonded, spun-bonded, needle-punched, carded, thermal bonded hydroentangled, meltblown, aperture print bonded, needled, wet-laid, dry-laid, and combinations thereof.

Other Adhesive Components

The present invention compositions may also include other adhesive components. These adhesive components, if present, are used in safe and adhesively effective amounts. The term "safe and adhesively effective amount" as used herein means an amount sufficient to provide adherence of a dental prosthesis to the palate and ridge of the oral cavity without toxicity to the user, damage to oral tissue, and alteration of the denture material.

Suitable adhesive components include a water-soluble hydrophilic colloid or polymer having the property of swelling upon exposure to moisture to form a mucilaginous mass. Such adhesive materials include natural gums, synthetic polymeric gums, adhesive materials commonly employed in denture stabilizing compositions and compatible with the subject AVE/MA copolymers, synthetic polymers, mucoadhesive polymers, hydrophilic polymers, saccharide derivatives, cellulose derivatives, and mixtures thereof. Examples of such materials include karaya gum, guar gum, gelatin, algin, sodium alginate, tragacanth, chitosan, polyethylene glycol, acrylamide polymers, carbopol, polyvinyl alcohol, polyvinyl acetate, polyamines, polyquarternary compounds, polybutenes, silicones, ethylene oxide polymers, polyvinylpyrrolidone, cationic polyacrylamide polymers. However, the organic crosslinker utilized in the formulation should not be included as an additional adhesive material in the same formulation.

Preferred are cellulose derivatives such as methylcellulose, sodium carboxymethylcellulose, hydroxyethylcellulose, hydroxypropylcellulose hydroxypropylmethylcellulose, carboxymethylcellulose. Most preferred are carboxymethylcellulose and sodium carboxymethylcellulose. In general, the other adhesive components may be present at a level of from about 0% to about 70%, preferably from about 10% to about 50%, and most preferably from about 20% to about 40%, by weight of the composition.

Other Ingredients

One or more toxicologically-acceptable plasticizers may also be included in the present compositions. The term "toxicologically-acceptable", as used herein, is used to describe materials that are suitable in their toxicity profile for administration to humans and/or lower animals. Plasticizers that may be used in the present compositions include dimethyl phthalate, diethyl phthalate, dioctyl phthalate, glycerin, diethylene glycol, triethylene glycol, Igepal, Gafac, sorbitol, tricresyl phosphate, dimethyl sebacate, ethyl glycolate, ethylphthalyl ethyl glycolate, o- and p-toluene ethyl sulfonamide, and mixtures thereof. Plasticizers may be present at a level of from about 0% to about 70%, preferably from about 0.1% to about 30%, by weight of the compositions.

The denture adhesive compositions may also be used as a denture adhesive and/or bioadhesive and comprise one or more therapeutic actives suitable for mucosal or topical administration. The phrase "suitable for mucosal or topical administration", as used herein, describes agents which are pharmacologically active when absorbed through internal mucosal surfaces of the body such as the oral cavity, or applied to the surfaces of the skin. Therapeutic actives may be present at a level of from about 0% to about 70%, by weight of the composition.

Therapeutic actives that are useful in these compositions include antimicrobial agents such as iodine, sulfonamides, bisbiguanides, or phenolics; antibiotics such as tetracycline, neomycin, kanamycin, metronidazole, or clindamycin; anti-inflammatory agents such as aspirin, acetaminophen, naproxen and its salts, ibuprofen, ketorolac, flurbiprofen, indomethacin, cimetidine, eugenol, or hydrocortisone; dentinal desensitizing agents such as potassium nitrate, strontium chloride or sodium fluoride; anesthetic agents such as lidocaine or benzocaine; anti-fungals; aromatics such as camphor, eucalyptus oil, and aldehyde derivatives such as benzaldehyde; insulin; steroids; and anti-neoplastics. It is recognized that in certain forms of therapy, combinations of these agents in the same delivery system may be useful in order to obtain an optimal effect. Thus, for example, an antimicrobial and an anti-inflammatory agent may be combined in a single delivery system to provide combined effectiveness.

The present denture adhesive compositions may also comprise coating which is sticky to dry dentures and, if present, will be placed on one side of the denture adhesive composition. Compositions suitable for use as the adhesive layer include polybutenes, silicones, rubbers, petrolatum, natural polymers, synthetic polymers, and mixtures thereof. The adhesive layer may be present at a level of from about 0% to about 70%, and preferably from about 0.5% to about 20%, by weight of the composition.

Other suitable ingredients include silicon dioxide, colorants, preservatives such as methyl and propyl parabens; thickeners; and delivery vehicles such as liquid petrolatum, petrolatum, mineral oil and glycerin. Preferred are polyethylene glycol, silicon dioxide, and petrolatum. Colorants, preservatives, thickeners and delivery vehicles may be present at levels of from about 0% to about 20%, by weight of the composition.

The compositions of the present invention may also include one or more components which provide flavor, fragrance, and/or sensate benefit. Suitable components include natural or artificial sweetening agents, menthol, menthyl lactate, wintergreen oil, peppermint oil, spearmint oil, leaf alcohol, as well as coolants 3-1-menthoxypropane-1,2-diol and paramenthane carboxyarnide agents such as N-ethyl-p-menthane-3-carboxamide which is described in U.S. Pat. No. 4,136,163 to Watson et. al., which is incorporated by reference herein in its entirety. These agents may be present at a level of from about 0% to about 50%, by weight of the composition.

Process for Preparation of the Composition

The present compositions can be prepared by any of the methods or combination of methods which follow. The term "mixture", as used herein, refers to a solution, slurry, or suspension.

The lower alkyl vinyl ether maleic anhydride copolymers can be obtained either from commercial suppliers under the trade names disclosed previously or by copolymerization of a lower alkyl vinyl ether monomer with maleic anhydride to yield the corresponding lower alkyl vinyl ether-maleic anhydride copolymer which is readily hydrolyzable to the acid copolymer.

Covalent crosslinking of AVE/MA copolymer is achieved though esterification of the maleic anhydride unit of the copolymer. For a solution process, disperse the lower alkyl vinyl either/maleic anhydride copolymer in a suitable solvent containing the organic crosslinker. The reaction occurs at elevated temperature. For aqueous medium, the temperature range of from about 45° C. to about 100° C. may be used. Preferably, the temperature is in the range of from about 65° C. to about 100° C., and most preferably from about 85° C. to about 95° C. The polymer may be neutralized during or after esterification. The polymer may also be crosslinked with polyvalent metal ions in addition to the polyol during or after esterification. The resultant polymer may be dried either in a forced air mechanical convection oven or a drum dryer. After drying, the sticky polymer turns into brittle flakes which can be easily peeled off from the drying surface and further grounded to a fine powder as desired.

Covalent crosslinking of AVE/MA copolymer or its partial salts can also be made during curing of a solids mixture of the copolymer or its salts and the organic crosslinker. Curing can be achieved in a conventional heating element or a microwave source. For a conventional heating element, a temperature range of from about 90° C. to about 150° C. is preferred. Most preferred is a temperature range of from about 110° C. to about 130° C. Curing of the copolymers after the solution processes is preferred. Without being bound by theory, it is believed that during the curing process, the anhydride forms from the un-neutralized carboxyl group, therefore, esterification of the anhydride by an adjacent organic crosslinker could occur.

The adhesive components (partial salt copolymers and other adhesive components, if present) may be coated on the non-adhesive self-supporting layer using various methods. These include: (a) wetting the non-adhesive self-supporting layer with water, uniformly sifting the adhesive component powder(s) onto the wet layer and then rewetting the layer with water; (b) dissolving the adhesive component(s) in water and/or other solvent(s) and coating the resulting mixture onto the layer; (c) coating the layer with the mixture produced during Gantrez® processing; (d) incorporating the adhesive component(s) into the layer as the layer is being formed; and (e) dissolving the adhesive component(s) in water and/or other solvent(s), wetting/coating the resulting mixture onto the layer, and uniformly sifting one or more adhesives in powder form onto the wet/coated layer and optionally re-coating/re-wetting the layer with the mixture and/or water; (f) the method of step (e) repeated multiple times; and (g) any combination of the methods in (a) through (f) above.

As disclosed above, the adhesive components may be dissolved in water and/or other solvents and the resulting mixture coated onto the layer. Solvents for the AVE/MA polymers include water and/or alcohols such as methanol, propanol, isopropanol, ethanol, butanol, 1,4-butanediol, cyclohexanol, and diethylene glycol; ethers or ether alcohols such as tetrahydrofuran, ethylene glycol monomethyl ether, diethylene glycol monomethyl ether, dioxane, and ethyl ether; esters such as methyl acetate, ethyl acetate and sec-butyl acetate; aldehydes, ketones or ketone-alcohols such as benzaldehyde, formaldehyde solution, methyl ethyl ketone, diacetone alcohol, acetone, cyclohexanone, mesityl oxide, and methyl isobutyl ketone; lactams or lactones such as N-methyl-2-pyrrolidone, N-vinyl-2-pyrrolidone, 2-pyrrolidone, and butyrolactone; hydrocarbons such as benzene, toluene, xylene, hexane, mineral spirits, mineral oil, and gasoline; chlorinated hydrocarbons such as carbon tetrachloride, chlorobenzene, chloroform, ethylene dichloride, methylene chloride; nitroparaffins such as nitroethane, and nitromethane; mercaptans such as thiophenol and 2-mercapto-1-ethanol; and others such as acetic acid, pyridine and dimethyl formamide.

Preferred solvents for the AVE/MA polymers are water, methanol, propanol, isopropanol, tetrahydrofuran, methyl acetate, benzaldehyde, formaldehyde solution, methyl ethyl ketone, diacetone alcohol, N-methyl-2-pyrrolidone, N-vinyl-2-pyrrolidone, dimethyl formamide and mixtures thereof. Compounds commonly used as plasticizers can also be used as solvents for the AVE/MA polymers. Such plasticizers include dimethyl phthalate, diethyl phthalate, dioctyl phthalate, glycercin, diethylene glycol, triethylene glycol., Igepal® CO-630, Gafac® RE-610, Sorbitol, tricresyl phosphate, dimethyl sebacate, ethyl glycolate, ethylphthalyl ethyl glycolate, and p-toluene ethyl sulfonamide.

Solvents for other adhesives such as carboxymethylcellulose ("CMC") which may be optionally included in the adhesive compositions include mixtures of water and water-miscible solvents such as ethanol and acetone. Solutions of low concentration can be made with up to 40% acetone and/or 50% alcohol. Other solvents which made be used include ethanolamines; ethylene glycol; glycerol; 1,2,6-hexanetriol; mono-, di-, and triacetin; 1,5-pentanediol; polyethylene glycol (molecular weight 600 or less); propylene glycol; and trimethylolpropane.

When the adhesive compositions are prepared by dissolving the adhesive component(s) in water and/or other solvents, various embodiments of the process includes: dissolving AVE/MA adhesives in one or more of the solvents for AVE/MA polymers; dissolving an optional adhesive in a suitable solvent and coating the resulting mixture onto the non-adhesive self-supporting layer and then optionally sifting one or more adhesives onto the coated layer. Coating the layer can be achieved by techniques commonly known in the art including extrusion, doctor blading, spraying, dipping, etc.

After the adhesive component(s) has been deposited on the layer by one of the means described above, the layer is then dried. Next, the denture adhesive composition is mechanically softened by running it through a ring-roller or micro-cracker or any other suitable means. The composition is then pressed smooth in a hydraulic press or flat-roller or other suitable means. The composition is then die-cut into denture shapes. These shapes may facilitate application of the composition to the dentures.

The following examples further describe and demonstrate embodiments within the scope of the present invention. The examples are given solely for the purpose of illustration and are not to be construed as limitations of the present invention, as many variations thereof are possible without departing from the spirit and scope of the invention.

EXAMPLE I

Place 2.85 grams of polyethylene glycol ("PEG") 300 and 1252.95 grams of purified water, USP at room temperature, into a 2 liter resin reaction kettle equipped with a high torque mixer with a built-in viscosity monitor. Mix for about 5 minutes at 300 rpm with a paddle stirring element. Slowly add 15.00 grams of poly (methyl vinyl ether/maleic anhydride) ("MVE/MA") copolymer or Gantrez® AN169 until the copolymer is well dispersed. Heat the resin reaction kettle with a temperature controlled water bath to 90° C. Maintain the reaction temperature between 85° C. and 95° C., and at a constant agitation rate of 300 rpm, until completion of esterification and hydrolysis reactions (indicated by transparent clarity of the reaction batch and increase in viscosity).

Separately, prepare a slurry containing 4.20 grams of calcium hydroxide and 225 grams of purified water, USP, in a beaker. Slowly add the slurry to the resin reaction kettle after completion of the esterification and hydrolysis reactions, and mix until completion of neutralization and crosslinking reactions (indicated by disappearance of insoluble calcium hydroxide and rise in pH measured in an aliquot of 1:10 (v/v) dilution). A typical pH of the resulting solution is around 5.4. The clarity of the finished batch is transparent.

Transfer the resulting solution to shallow stainless steel drying trays, and dry in a forced air mechanical convection oven at 60° C. for a sufficient time to evaporate the reaction medium (water) and remove the water from the polymer (about 18 to 24 hours). After drying, cure the copolymer in the same oven at about 120° C. for about 2 hours. The copolymer forms brittle flakes. Grind the flakes to a fine powder in a milling apparatus such as speed-rotor mill with an appropriate screen to define the mean particle size and its distribution. Typically, a 0.12 mm or 0.08 mm screen is used. The resulting adhesive copolymer yields a 60% neutralized partial calcium salt of MVE/MA copolymer covalently crosslinked with PEG 300. The PEG:COOH molar ratio is 5%.

Wet 58" by 20" of the non-adhesive self-supporting layer with water. Uniformly coat 150 grams of adhesive components (90 g Ca MVE/MA copolymer and 60 g carboxymethylcellulose) onto the layer and rewet the layer with water. Dry the layer. Mechanically soften the denture adhesive composition by ring-roller, and then smooth the composition on a hydraulic press. Cut the composition into denture-shaped wafers. Moisten the wafers and apply to the dentures. This wafer is peelable from the denture and forms a sticky seal that holds the dentures in place, does not ooze, and aids in preventing food from sticking between the dentures and gums.

Variations of Example I useful herein include:

(a) Substitution of 4.09 grams of polypropylene glycol 425 for 2.85 grams of PEG 300;

(b) Substitution of 4.62 grams of sodium hydroxide for 4.20 grams of calcium hydroxide.

(c) Substitution of 1.93 grams of 1,12-dodecanediamine for 2.85 grams of PEG 300.

(d) Elimination of the curing process.

EXAMPLE II

Place 1477.95 grams of purified water, and 2.85 grams of PEG 300 into a 2 liter resin reaction kettle equipped with a high torque mixer. Mix for about 5 minutes at 300 rpm with a paddle stirring element. Slowly add 4.20 grams of calcium hydroxide till the solid is well dispersed. Then slowly add 15.00 grams of MVE/MA copolymer or Gantrez® AN169 until the copolymer is well dispersed. Heat the resin reaction kettle with a temperature controlled water bath to 90° C. Maintain the reaction temperature between 85° C. and 95° C., and a constant agitation rate of 300 rpm, until completion of esterification and hydrolysis reactions (indicated by transparent clarity of the reaction batch and rise of pH to stabilization). Typical pH of the solution is around 5.4. The solution chemistry consists of esterification and hydrolysis of the maleic anhydride as well as neutralization and crosslinking of the maleic acid moiety with calcium hydroxide and calcium ion, respectively.

Repeat the same drying, curing, and milling procedures as described in Example I. The resulting adhesive copolymer yields a 60% neutralized partial calcium salt of MVE/MA copolymer covalently crosslinked with PEG 300 (PEG:COOH molar ratio is 5%). Repeat the procedures for preparing the non-adhesive self-supporting layer, as described in Example I.

Variations of Example II useful herein include:
(a) Substitutions set forth in Table II:

TABLE II

|   | PEG300 (gram) | PEG/COOH Molar Ratio (%) | Purified Water, USP (gram) |
|---|---|---|---|
| A | 1.50 | 2.5 | 1479.30 |
| B | 5.70 | 10.0 | 1475.10 |
| C | 7.20 | 12.5 | 1473.60 |

(b) Substitutions of varying average molecular weights of PEG, as set forth in Table III (Note the PEG:COOH molar ratio is kept at 5%):

TABLE III

|   | PEG (gram) | PEG Average Molecular Weight | Purified Water, USP (gram) |
|---|---|---|---|
| A | 1.95 | 200 | 1478.85 |
| B | 3.90 | 400 | 1476.90 |
| C | 5.70 | 600 | 1475.10 |
| D | 9.60 | 1000 | 1471.20 |

EXAMPLE III

Place 1413.59 grams of purified water and 11.41 grams of PEG 300 into a 2 liter resin reaction kettle equipped with a high torque mixer. Mix for about 5 minutes at 300 rpm with a paddle stirring element. Add 75.00 grams of 60% neutralized partial calcium salt of MVE/MA copolymer made from Gantrez® AN169 at an appropriate speed such that the salt is dispersed before it becomes fully hydrated. Heat the resin reaction kettle with a temperature controlled water bath to 90° C. Maintain the reaction temperature between 85° C. and 95° C. and a constant agitation rate of 300 rpm until no clumps are visible (1 to 3 hours).

Repeat the same drying, curing and milling procedures described in Example I. The resulting adhesive copolymer yields a 60% neutralized partial calcium salt of MVE/MA copolymer covalently crosslinked with PEG 300 (PEG:COOH molar ratio is 5%). Repeat the procedures for preparing the non-adhesive self-supporting layer, as described in Example I.

EXAMPLE IV

Metal cations and their corresponding percents of initial carboxyl groups of partial salt AVE/MA copolymers reacted, described in Table IV, can be utilized in the processes of Examples I–III to formulate mixed partial salts of MVE/MA copolymers crosslinked with PEG. For divalent metal cations, the appropriate metal oxide, hydroxide, carbonate or bicarbonate can be used. For trivalent metal cations, the sulfate salt is preferred.

TABLE IV

|   | % $Ca^{2+}$ | % $Mg^2$ | % $Zn^{2+}$ | % $Sr^2$ | % $Fe^3$ |
|---|---|---|---|---|---|
| A | 47.5 | — | 17.5 | — | — |
| B | — | 47.5 | 17.5 | — | — |
| C | 47.5 | — | 17.5 | — | 0.5 |
| D | — | 47.5 | 17.5 | — | 0.5 |
| E | 27.5 | — | 17.5 | 20.0 | — |
| F | 27.5 | — | 17.5 | 20.0 | 0.5 |
| G | — | 27.5 | 17.5 | 20.0 | — |
| H | — | 27.5 | 17.5 | 20.0 | 0.5 |

EXAMPLES V–IX

| Example # | Adhesive Component | Non-Adhesive Self-Supporting Layer |
|---|---|---|
| V | 47.5 Ca/17.5 Zn MVE/MA/PEG[b]+CMC[a] | Non-woven polyester |
| VI | 60 Ca MVE/MA/PEG[c]+CMC[a] | Polypropylene |
| VII | 47.5 Ca/17.5 Zn MVE/MA/PEG[b]+CMC[a] | Non-woven rayon |
| VIII | 47.5 Ca/17.5 Zn/0.5 Fe MVE/MA/PEG[d]+CMC[a] | Cloth |
| IX | 65 Na MVE/MA/PEG[e]+CMC[a] | Paper |

[a] Carboxy methyl cellulose.
[b] Methyl vinyl ether-maleic acid partial salt neutralized with 47.5% calcium and 17.5% zinc, and covalently crosslinked with PEG. PEG:COOH molar ratio = 5%.
[c] Methyl vinyl ether-maleic acid partial salt neutralized with 60% calcium, and covalently crosslinked with PEG. PEG:COOH molar ratio = 5%.
[d] Methyl vinyl ether-maleic acid partial salt neutralized with 47.5% calcium, 17.5% zinc, and 0.5% ferric iron, and covalently crosslinked with PEG. PEG:COOH molar ratio = 4%.
[e] Methyl vinyl ether-maleic acid partial salt neutralized with 65% sodium, and covalently crosslinked with PEG. PEG:COOH molar ratio = 10%.

The adhesive component in Examples V–IX may also include 0.1 to 15 grams of silicon dioxide.

Examples V–IX are prepared as follows. Wet 58" by 20" of the non-adhesive self-supporting layer with water. Uniformly coat 150 grams of the adhesive component (90 g MVE/MA/PEG partial salt copolymer and 60 g CMC) onto the layer and rewet the layer with water. Dry the layer. Mechanically soften the denture adhesive composition by ring-roller, and then smooth the composition on a hydraulic press. Cut the composition into denture-shaped wafers. Moisten the wafers and apply to the dentures. This wafer is peelable from the denture and forms a sticky seal that holds the dentures in place, does not ooze, and aids in preventing food from sticking between the dentures and gums.

What is claimed is:
1. A denture adhesive composition comprising:
  a) at least one non-adhesive self-supporting layer; and
  b) a partial salt of a lower alkyl vinyl ether-maleic acid copolymer, the partial salt copolymer comprising carboxyl groups, of which from about 50% to about 95% are neutralized by one or more metal cations; wherein the partial salt copolymer is covalently crosslinked with an organic crosslinker and wherein the molar ratio of the organic crosslinker to carboxyl groups, prior to neutralization by the metal cations, is from about 0.1 to about 30%.

2. The denture adhesive composition according to claim 1 wherein the non-adhesive self-supporting layer is selected from the group consisting of polyester, polypropylene, nylon, rayon, polyethylene oxide, cellulose acetate, cellulose derivatives, cloth, fibrous fleece, paper, plastic, leather, microcrystalline wax, synthetic fibers, natural fibers, and mixtures thereof.

3. The denture adhesive composition according to claim 1 wherein the non-adhesive self-supporting layer is in a physical form selected from the group consisting of non-woven, woven, continuous, chopped, and combinations thereof.

4. The denture adhesive composition according to claim 1 wherein the non-adhesive self-supporting layer is formed by a process selected from the group consisting of un-bonded, spraybonded, spun-bonded, needle-punched, carded, thermal bonded hydroentangled, meltblown, aperture print bonded, needled, wet-laid, dry-laid, and combinations thereof.

5. The denture adhesive composition according to claim 1 wherein the organic crosslinker is selected from the group consisting of polyols, polyamines and compounds containing at least two mixed functional groups.

6. The denture adhesive composition according to claim 5 wherein the polyol is polyethylene glycol having an average molecular weight of from about 200 to about 600.

7. The denture adhesive composition according to claim 6 wherein the metal cations are monovalent, divalent or polyvalent metal cations selected from the group consisting of calcium, sodium, magnesium, potassium, ammonium, zinc, strontium, iron, aluminum, and mixtures thereof.

8. The denture adhesive composition according to claim 7 wherein the molar ratio of the organic crosslinker to the carboxyl groups, prior to neutralization by the metal cations, is from about 1% to about 20%.

9. A denture adhesive composition comprising:
   a) at least one non-adhesive self-supporting layer; and
   b) a partial salt of a lower alkyl vinyl ether-maleic acid copolymer, the partial salt copolymer comprising carboxyl groups, of which from about 50% to about 95% are neutralized by from 10% to about 65% zinc cations and from about 10% to about 75% calcium cations; wherein the partial salt copolymer is covalently crosslinked with an organic crosslinker and wherein the molar ratio of the organic crosslinker to the carboxyl groups, prior to neutralization by the metal cations, is from about 0.1% to about 30%.

10. The denture adhesive composition according to claim 9 wherein the non-adhesive self-supporting layer is selected from the group consisting of polyester, polypropylene, nylon, rayon, polyethylene oxide, cellulose acetate, cellulose derivatives, cloth, fibrous fleece, paper, plastic, leather, microcrystalline wax, synthetic fibers, natural fibers, and mixtures thereof.

11. The denture adhesive composition according to claim 9 wherein the non-adhesive self-supporting layer is in a physical form selected from the group consisting of non-woven, woven, continuous, chopped, and combinations thereof.

12. The denture adhesive composition according to claim 9 wherein the non-adhesive self-supporting layer is formed by a process selected from the group consisting of un-bonded, spraybonded, spun-bonded, needle-punched, carded, thermal bonded hydroentangled, meltblown, aperture print bonded, needled, wet-laid, dry-laid, and combinations thereof.

13. The denture adhesive composition according to claim 9 wherein the organic crosslinker is polyethylene glycol having an average molecular weight of 300.

14. The denture adhesive composition according to claim 13 wherein the molar ratio of the organic crosslinker to the carboxyl groups, prior to neutralization by the metal cations, is from about 2% to about 10%.

15. The denture adhesive composition according to claim 14 further comprising an additional adhesive component selected from the group consisting of natural gums, synthetic polymers, mucoadhesive polymers, hydrophilic polymers, natural polymers, saccharide derivatives, cellulose derivatives, and mixtures thereof.

16. The denture adhesive composition according to claim 15 wherein the cellulose derivatives are selected from the group consisting of hydroxyethylcellulose, sodium carboxymethylcellulose, carboxymethylcellulose, and mixtures thereof.

17. The denture adhesive composition according to claim 16 further comprising a toxicologically-acceptable plasticizer.

18. The denture adhesive composition according to claim 17 wherein the plasticizer is selected from the group consisting of dimethyl phthalate, diethyl phthalate, dioctyl phthalate, glycerin, diethylene glycol, triethylene glycol, Igepal, Gafac, sorbitol, tricresyl phosphate, dimethyl sebacate, ethyl glycolate, ethylphthalyl ethyl glycolate, o- and p-toluene ethyl sulfonamide, and mixtures thereof.

19. The denture adhesive composition according to claim 18 further comprising one or more of ingredients selected from the group consisting of colorants, preservatives, thickeners, delivery vehicles, flavors, fragrances, and sensates.

20. A process for preparation of the denture adhesive composition according to claims 1 comprising the steps of:
   a) creating an aqueous dispersion of a lower alkyl vinyl ether-maleic anhydride copolymer and an organic crosslinker;
   b) heating the dispersion wherein the lower alkyl vinyl ether-maleic anhydride copolymer and the organic crosslinker become covalently crosslinked through esterification of the copolymer;
   c) adding a metal cation slurry to the dispersion in (b) wherein a partial salt of the copolymer is formed;
   d) drying the partial salt;
   e) curing the partial salt at an elevated temperature;
   f) mixing the partial salt with water and/or one or more solvents to create a mixture; and
   g) applying the mixture onto a non-adhesive self-supporting layer.

* * * * *